United States Patent [19]

Bull

[11] Patent Number: 4,590,286
[45] Date of Patent: May 20, 1986

[54] PROCESS FOR EPOXIDIZING AN OLEFIN
[75] Inventor: Randy A. Bull, Hopewell, N.J.
[73] Assignee: FMC Corporation, Philadelphia, Pa.
[21] Appl. No.: 791,811
[22] Filed: Oct. 28, 1985
[51] Int. Cl.$^4$ ............................................ C07D 301/16
[52] U.S. Cl. ................................................. 549/526
[58] Field of Search ........................................ 549/526

Primary Examiner—Paul R. Michl
Assistant Examiner—Alex H. Walker
Attorney, Agent, or Firm—R. E. Elden; R. L. Andersen

[57] ABSTRACT

The present invention concerns a process for epoxidizing an olefin to an oxirane by forming a monopercarboxylic acid in-situ by reacting a cyclic anhydride of a polybasic acid with hydrogen peroxide in the presence of a basic catalyst and recovering the oxirane as a distillate.

16 Claims, No Drawings

PROCESS FOR EPOXIDIZING AN OLEFIN

The invention is a process for epoxidizing a substantially anhydrous solution of an olefin with a peroxycarboxylic acid in a solvent having a high boiling point. The peroxycarboxylic acid is formed in-situ by the reaction of hydrogen peroxide with a cyclic anhydride of a polycarboxylic acid and the oxirane formed is recovered as a distillate. Optionally, the polycarboxylic acid coproduct may be dehydrated in the residual solution to a cyclic anhydride and recycled.

Swern, "Organic Peroxides," Vol. II, Wiley-Interscience, New York (1971) at pages 357 to 375, discloses that the reaction of an olefin, a compound containing at least one carbon-carbon double bond, with a peroxycarboxylic acid is a well known general method for forming an oxirane. Swern teaches that a cyclic anhydride of a polycarboxylic acid, for example phthalic anhydride, succinic anhydride or 1,2-cyclohexanedicarboxylic anhydride, is useful for such epoxidizations. In each of the reference examples the cyclic anhydride can be reacted either in-situ with hydrogen peroxide to form a monoperoxydicarboxylic acid, or the peroxyacid can be preformed. Swern further discloses that an epoxidation employing a monoperoxydicarboxylic acid, for example, monoperphthalic acid, is usually conducted in a solvent in which the phthalic acid coproduct is insoluble. As a consequence, the phthalic acid precipitates and is not available in solution to catalyze unwanted ring-opening of the oxirane ring.

The in-situ process in the Swern reference is the process of U.S. Pat. No. 3,155,638. The in-situ process forms a monoperoxydicarboxylic acid by reacting hydrogen peroxide in the absence of a catalyst with the cyclic anhydride of an aliphatic or aromatic polycarboxylic acid. The process reaction is very slow without the usual strong acid catalyst, requiring ten hours or more for completion. Such a slow reaction rate is undesirable. In addition, the reference teaches using a solvent in which the polycarboxylic acid coproduct is insoluble, adding the disadvantage of an expensive solids handling step.

U.S. Pat. No. 3,510,512, teaches that a stable monoperoxyphthalic acid can be prepared by reacting a solution of phthalic anhydride and hydrogen peroxide in the presence of an alkaline catalyst, acidifying the reaction mixture, and separating the solid monoperoxyphthalic acid from the reaction mixture. The process is not desirable because of the additional steps required to make the preformed percarboxylic acid and the cost of the solids handling steps.

The present process avoids the problems of the prior art in epoxidizing an olefin to form an oxirane by the steps of (a) forming a reaction mixture by incorporating an olefin, a cyclic anhydride of a polybasic carboxylic acid, and a basic catalyst into a nonaqueous inert solvent having a boiling point substantially greater than the boiling point of the oxirane of the olefin, the anhydride being incorporated in an amount sufficient to maintain the reaction mixture substantially anhydrous, (b) incorporating hydrogen peroxide into the reaction mixture at a rate controlled to avoid accumulating a substantial excess of hydrogen peroxide in the reaction mixture thereby converting at least part of the olefin to the corresponding oxirane and at least part of the cyclic anhydride to a corresponding polybasic carboxylic acid, and (c) recovering the oxirane as a distillate from the product of step (b) and leaving a residue of polybasic carboxylic acid in inert solvent.

Optionally, the anhydride may be regenerated by heating the residue to dehydrate the polybasic acid to the anhydride and the resulting solution of anhydride in the inert solvent may be recycled.

Although not critical, it is desirable to use a reaction mixture in which all components are soluble so that a single phase, homogeneous mixture results. It is critical that the solvent have a higher boiling point than the product oxirane to permit recovery of the oxirane from the reaction mixture as a distillate. This avoids expensive solids handling steps and permits the conversion of the acid to the anhydride reactant. High boiling solvents that result in a homogeneous reaction mixture include sulfolane, pyrrolidone, N-alkylpyrrolidones such as N-methyl-2-pyrrolidone and substituted ureas such as tetrabutyl ureas. Preferred solvents are sulfolane or N-methyl-2-pyrrolidone as both are high boiling, oxidatively stable, and readily available.

The use of a cyclic anhydride of a polybasic acid is critical. Suitable anhydrides include and polycarboxylic acid anhydride which is soluble in the organic solvent in both the anhydride and the acid forms, however, it is not necessary for the polycarboxylic acid to be completely dissolved, but it may be present in an amount sufficient to form a slurry. Commonly available dicarboxylic acid anhydrides such as maleic, succinic, phthalic and substituted phthalic anhydrides are desirable. For reasons of economy, oxidative stability, reactivity and solubility phthalic anhydride is preferable. The amount of anhydride used should be an amount sufficient to react with all of the hydrogen peroxide added to form the peroxyacid and also sufficient to react with all the water present in or added to the reaction mixture. One skilled in the art will recognize that cyclic anhydrides of tricarboxylic and tetracarboxylic acids are also suitable for the process.

It is well known according to Kirk-Othmer, "Encyclopedia of Chemical Technology," Third Edition, Vol. 9, pages 251 to 266, that epoxidation is the formation of cyclic three-membered ethers (oxiranes) by the reaction of peracids and hydrogen peroxide with olefinic double bonds. For the purpose of this invention, the term olefin is used to indicate any alkene or compound having such olefinic double bonds. It is critical for the present invention that the oxirane of the olefin has a boiling point lower than that of the solvent employed and can be distilled from the solvent without decomposition. Preferably an olefin selected from the group consisting of propylene, butene, pentene, hexene, octene, cyclobutene, cycloheptene, cyclohexene and cyclooctene, styrene, allylic esters, allyl alcohol, terpenes, vinylcyclohexene and butadiene. It is not necessary that the olefin contains only carbon and hydrogen but it may contain another functional group so long as the functional group does not interfere with the epoxidation or cause the formation of unwanted by-products.

The formation of the monoperoxycarboxylic acids of the present invention requires the presence of an organic or inorganic base as a catalyst. Any amount of base may be used but it is desirable to use the base in a catalytic amount with respect to the amount of hydrogen peroxide used. Preferably no more than 50 mol % of base is used compared to the hydrogen peroxide used. The base need not be soluble in the reaction mixture. Suitable inorganic bases are the alkali metal carbonates and bicarbonates such as $Li_2CO_3$, $LiHCO_3$, $Na_2CO_3$, $NaHCO_3$, $K_2CO_3$, and $KHCO_3$, alkali metal hydroxides and borate salts such as $Na_2B_4O_7$. Perborate salts may also be used to serve as both a source of hydrogen peroxide and a basic catalyst or may be mixed with hydrogen peroxide. Organic bases that may be used are tertiary amines and their N-oxides and heterocyclic nitrogen compounds such as pyridine, pyridine-N-oxide, quinoline, quinoline-N-oxide, N-methylmorpholine, or N-methylmorpholine-N-oxide. If the solvent used is sufficiently basic such as N-methyl-2-pyrrolidone, no additional base catalyst is necessary. Although it is preferable that the base used be soluble in the reaction mixture it is not a requirement. For example, $Na_2CO_3$ is effective when slurried as a solid in the reaction medium.

The reaction conditions for the process of the present invention are not extreme. The reaction temperatures required should be sufficient to keep the solution liquid and need not be higher than 120° C. It is preferable to keep the reaction temperature between 30° C. and 100° C. and most preferable to keep the reaction temperature between 50° C. and 80° C. to minimize peracid and product decomposition.

It is critical for the present invention for the hydrogen peroxide to be incorporated into the reaction mixture at a rate controlled to avoid accumulating a substantial excess of hydrogen peroxide which may form a hydroperoxide or open the oxirane ring. This critical rate can easily be determined by one skilled in the art without undue experimentation by spot tests with sodium iodide or titanium dioxide.

The rate of hydrogen peroxide addition to the reaction mixture is dependent upon the rate of formation of the monoperoxycarboxylic acid. An uncatalyzed reaction of hydrogen peroxide with an anhydride may require hydrogen peroxide addition over a period of four hours or more, and for phthalic anhydride in sulfolane, the formation of the peracid, monoperoxyphthalic acid, may not take place to any appreciable extent. However, with a basic catalyst most of the hydrogen peroxide will react to form a peracid in less than one to two hours, thus a more rapid rate of hydrogen peroxide addition is possible. If hydrogen peroxide is added faster than the rate of peracid formation there will be a build-up of free hydrogen peroxide in the reaction medium which, if sufficient, can lead to the formation of the undesired by-products. The rate of hydrogen peroxide addition is clearly dependent upon factors such as the temperature, the solvent and the anhydride and can be easily determined by experiment.

The concentration of the aqueous hydrogen peroxide used is not critical so long as the amount of polycarboxylic acid anhydride used is sufficient to react with all of the hydrogen peroxide and water added with it. Thus it is convenient and preferable to use hydrogen peroxide of at least 50% and more preferable to use hydrogen peroxide of at least 70% concentration by weight so that less water is added with the hydrogen peroxide and therefore less anhydride will be required.

The amount of hydrogen peroxide incorporated into the reaction mixture is desirably between 0.3 and 2 mols of hydrogen peroxide per mol of olefin. It is preferable to incorporate about 0.4 to 1.1 mol of hydrogen peroxide per mol of olefin for efficiency of reaction and to prevent excessive oxidation. A significantly less than stoichiometric amount of hydrogen peroxide would result in the need to recycle large amounts of unreacted olefin while a large excess of hydrogen peroxide may produce undesirable by-products. However, it may be desirable to incorporate a slight excess into the reaction mixture to compensate for decomposition.

The present invention provides for a simplified process for the isolation of product and regeneration of the dicarboxylic acid anhydride without distilling or processing the bulk of the solvent. Because the solvent has a higher boiling point than the products of the reaction the product may be distilled selectively from the reaction mixture. Any residual olefin starting material may also be distilled if its boiling temperature is lower than that of the solvent. At sufficiently high temperatures the polycarboxylic acid which is formed as a by-product of the reaction can be dehydrated in solution to the anhydride.

The process of the present invention may be practiced either as a batch process or as a continuous process. In either option it is particularly desirable to regenerate the poybasic acid to the anhydride to eliminate a need to recover the polybasic acid as a coproduct.

The following nonlimiting examples are presented to illustrate the best mode of practicing the present invention. The olefins used in the examples are C6 to C8 olefins to simplify the comparisons although it is clear from the prior art that any C4 to C30 alkene is suitable. The inventive examples are indicated by numerals, the comparative examples by letters.

EXAMPLES

1. A 200 ml flask equipped with an overhead mechanical stirrer was charged with 80 mL purified sulfolane, 13.51 g (91 mmol) phthalic anhydride, 6.64 g (81 mmol) cyclohexene, and 2.12 g (20 mmol) $Na_2CO_3$. The mixture was heated to 50° C. with stirring and 1.92 g (40 mmol) 70.75 wt % $H_2O_2$ added over 50 minutes. The reaction was stirred for an additional hour at the reaction temperature, at which point the reaction was found to contain 0.48 mmol active oxygen, stated as $H_2O_2$, and 1.22 g (12.4 mmol) cyclohexene oxide for a yield of 31% based on the H O consumed.

2. Example 1 was repeated but the reaction temperature was 40° C. and the time of reaction after completion of H O addition was 20 minutes. At the end of the reaction 3.0 mmol $H_2O_2$ remained and 2.38 g (24.2 mmol) cyclohexene oxide were formed for a yield of 65%.

3. A 200 ml flask equipped with an overhead mechanical stirrer was charged with 80 mL sulfolane, 13.51 g (91 mmol) phthalic anhydride, and 2.12 g (20 mmol) $Na_2CO_3$. The reaction mixture was heated to 40° C. and 1.92 g (40 mmol) 70.75 wt % $H_2O_2$ was added over 15 minutes. This was immediately followed by the addition of 6.64 g (81 mmol) cyclohexene over a period of 30 minutes. The reaction was stirred for an additional 15 minutes after cyclohexene addition. The final mixture continued 0.27 mmol unreacted $H_2O_2$ and 1.87 g (19.1 mmol) cyclohexene oxide for a yield of 48%.

4. A 200 ml flask equipped with an overhead mechanical stirrer was charged with 80 mL sulfolane, 13.51 g (91 mmol) phthalic anhydride, 8.82 g (80 mmol) cyclooctene, and 1.06 g (10 mmol) $Na_2CO_3$. The mixture was heated to 50° C. with stirring and 1.92 g (40 mmol) 7.75 wt % $H_2O_2$ added over one hour. The reaction mixture was stirred for an additional 15 minutes. The reaction contained 2.28 mmol unreacted $H_2O_2$ and 4.03 g (32 mmol) cyclooctene oxide for a yield of 85%.

5. Example 4 was repeated using as the olefin 8.98 g (80 mmol) 1-octene. At the end of the reaction 8.04 mmol residual H$_2$O$_2$ remained and 2.40 g (18.7 mmol) 1,2-epoxyoctane were formed for a yield of 59%.

6. Example 4 was repeated using 80 mL N-methyl-2-pyrrolidone as the solvent in place of sulfolane. The final reaction mixture contained 2.61 mmol unreacted H$_2$O$_2$ and 4.10 g (32.5 mmol) cyclooctene oxide for a yield of 87%.

7. Example 4 was repeated using 80 mL diglyme as solvent in place of sulfolane. The final reaction mixture contained 7.17 mmol unreacted H$_2$O$_2$ and 3.32 g (26.3 mmol) cyclooctene oxide for a yield of 80%.

8. Example 5 was repeated using 80 mL N-methyl-2-pyrrolidone as solvent in place of sulfolane. After reaction the final reaction mixture contained 20.71 mmol unreacted H$_2$O$_2$ and 0.85 g (6.62 mmol) 1,2-epoxyoctane for a yield of 34%.

9. Example 6 was repeated using 6.64 g (81 mmol) cyclohexene in place of cyclooctene, with a reaction temperature of 40° C. The final reaction mixture contained 7.04 mmol unreacted H$_2$O$_2$ and 1.93 g (19.7 mmol) cyclohexene oxide for a yield of 60%.

10. Example 6 was repeated using 0.95 g (10 mmol) pyridine-N-oxide in place of Na$_2$CO$_3$. The final reaction mixture contained 13.64 mmol unreacted H$_2$O$_2$ and 2.61 g (20.7 mmol) cyclooctene oxide for a yield of 78%.

BASE CATALYZED MONOPEROXYPHTHALIC ACID FORMATION

A. The effect of a base to catalyze peracid formation was demonstrated with 0.74 g (5 mmol) phthalic anhydride and 75 L (2 mmol) 70 wt % hydrogen peroxide dissolved in 10 mL sulfolane in each of two flasks. One flask was heated to 40° C. and the other to 60° C. and the mixtures analyzed for monoperoxyphthalic acid content, using the procedure of Greenspan and MacKellar (Anal. Chem, 1948, 20, 1061). Analysis indicated the peroxyacid concentration at 40° C. and 60° C. respectively to be 0.33 mmol and 0.41 mmol after 30 minutes, 0.24 mmol after 90 minutes, and 0.08 mmol and 0.11 mmol after 16 hours.

B. An experiment similar to comparative Example A was carried out with 1.48 g (10 mmol) phthalic anhydride and 0.5 mL (5 mmol) 30 wt % hydrogen peroxide in 20 mL sulfolane. After 30, 60 and 90 minutes, respectively, at 25° C. the mixture contained 0.05, 0.21 and 0.15 mmol of monoperoxyphthalic acid.

11. A mixture of 3.70 g (25 mmol) phthalic anhydride, 0.36 mL (10 mmol) 73 wt % hydrogen peroxide, and 0.21 g (2 mmol) Na$_2$CO$_3$ were placed in 40 mL sulfolane and the mixture heated to 60° C. After, 30, 60 and 90 minutes the mixtures contained, respectively, 7.9, 7.4 and 6.1 mmol monoperoxyphthalic acid.

12. A mixture of 7.41 g (50 mmol) phthalic anhydride and 6.92 g (45 mmol) sodium perborate tetrahydrate were placed in 80 mL sulfolane and the stirred mixture heated to 65° C. After 60 minutes the mixture contained 18.2 mmol monoperoxyphthalic acid.

C. Example 11 was repeated with 0.88 g (20 mmol) HBO$_2$ in place of Na$_2$CO$_3$. After 30, 60 and 90 minutes, respectively, the mixture contained 0.7, 0.7 and 0.8 mmol monoperoxyphthalic acid.

13. It was demonstrated that a solvent could function as a catalyst by placing 3 g (20 mmol) phthalic anhydride and 0.37 mL (10 mmol) 71 wt % hydrogen peroxide in 20 mL N-methyl-2-pyrrolidone, a slightly basic organic solvent. The mixture was heated to 50° C. and after 15, 45 and 75 minutes the mixture was found to contain 1.5, 2.0 and 2.9 mmol monoperoxyphthalic acid, respectively.

14. Example 13 was repeated with the addition of 0.32 g (4 mmol) pyridine added to the reaction mixture. At 15 and 45 minutes the mixture contained 3.8 and 3.2 mmol monoperoxyphthalic acid, respectively.

15. Example 13 was repeated with 0.19 g (2 mmol) pyridine-N-oxide. The mixture contained 3.6 and 5.9 mmol monoperoxyphthalic acid at 15 and 45 minutes, respectively.

DEHYDRATION OF PHTHALIC ACID

16. In-situ dehydration of phthalic acid was demonstrated by heating a solution of 9 g phthalic acid in 80 mL N-methyl-2-pyrrolidone to reflux under vaccum. IR spectra recorded at 2 and 4 hours showed the increasing presence of phthalic anhydride, as evidenced by the growth of peaks at 1930 and 1800 cm$^{-1}$. These peaks were attributed to the anhydride and are not present in the IR spectrum of phthalic acid.

DISTILLATION OF OXIRANE FROM REACTION MIXTURE

17. The reaction product mixture of Example 2 was subjected to a vacuum distillation of 0.7 to 0.9 kPa. At 30° C. a fraction distilled that was found to contain cyclohexene (60%), cyclohexene oxide (37%), and sulfolane (1.4%), the remainder being traces of unidentified material. The distillation pot contained traces of cyclohexene and cyclohexene oxide but predominantly consisted of sulfolane (89%). This demonstrates the selective distillation of products and excess reactants from a reaction mixture.

I claim:
1. A process for epoxidizing an olefin to form the corresponding oxirane comprising the steps of:
   (a) forming a reaction mixture by incorporating an olefin, a cyclic anhydride of a polybasic carboxylic acid, and a basic catalyst into a nonaqueous inert solvent, said solvent having a boiling point substantially greater than the boiling point of the oxirane of the olefin, and said anhydride being incorporated in an amount sufficient to maintain the reaction mixture substantially anhydrous,
   (b) incorporating hydrogen peroxide into the reaction mixture at a rate controlled to avoid accumulating a substantial excess of hydrogen peroxide in the reaction mixture thereby converting at least part of the olefin to the corresponding oxirane and at least part of the cyclic anhydride to a corresponding polybasic carboxylic acid, and
   (c) recovering the oxirane as a distillate from the product of step (b) and leaving a residue solution of polybasic carboxylic acid in inert solvent.

2. The process of claim 1 with the added steps of heating residue from step (c) sufficiently to convert at least part of the polybasic carboxylic acid in the residue to a solution of a cyclic anhydride of a polybasic acid in the solvent and recycling the solution of cyclic anhydride as part of the reaction mixture.

3. The process of claim 1 wherein the solvent is a compound selected from the group consisting of sulfolane, pyrrolidone, N-methyl-2-pyrrolidone and tetrabutyl urea, the olefin is selected from the group consisting of propylene, butene, pentene, hexene, octene, cyclobutene, cycloheptene, cyclohexene and cyclooctene, styrene, allylic esters, allyl alcohol, terpenes, vinylcyclohexene and butadiene and the cyclic anhydride is phthalic anhydride.

4. The process of claim 2 wherein the solvent is a compound selected from the group consisting of sulfolane, pyrrolidone, N-methyl-2-pyrrolidone and tetrabutyl urea, propylene, butene, pentene, hexene, octene, cyclobutene, cycloheptene, cyclohexene and cyclooctene, styrene, allylic esters, allyl alcohol, terpenes, vinylcyclohexene and butadiene and the cyclic anhydride is phthalic anhydride.

5. The process of claim 1 in which between 0.3 and 2 mols of hydrogen peroxide is incorporated into the reaction mixture per mol of the olefin.

6. The process of claim 1 in which between 0.4 and 1.10 mols of hydrogen peroxide is incorporated into the reaction mixture per mol of the olefin.

7. The process of claim 2 in which between 0.4 and 1.10 mols of hydrogen peroxide is incorporated into the reaction mixture per mol of the olefin.

8. The process of claim 3 in which between 0.4 and 1.10 mols of hydrogen peroxide is incorporated into the reaction mixture per mol of the olefin.

9. A process for oxidizing an olefin selected from the group consisting of propylene, butene, pentene, hexene, octene, cyclobutene, cycloheptene, cyclohexene and cyclooctene, styrene, allylic esters, allyl alcohol, terpenes, vinylcyclohexene and butadiene to an oxirane comprising:

(a) forming a reaction mixture by incorporating the olefin, a cyclic anhydride of a polybasic acid selected from the group consisting of maleic anhydride, succinic anhydride, phthalic anhydride and substituted phthalic anhydride, a basic catalyst into an inert solvent, the inert solvent having a boiling point substantially greater than the boiling point of the corresponding oxirane, and the cyclic anhydride being incorporated in an amount sufficient to maintain the reaction mixture substantially anhydrous, (b) incorporating hydrogen peroxide into the reaction mixture from step (a), the hydrogen peroxide being incorporated at a rate controlled to avoid accumulating a substantial excess of hydrogen peroxide in the reaction mixture, and maintaining the temperature thereof between 30° C. and 100° C. for a sufficient time to convert the olefin to the oxirane and the anhydride to the corresponding polybasic acid, (c) recovering the oxirane as a distillate from the product of step (b), leaving a residue polybasic acid in the solvent, (d) regenerating the cyclic anhydride of the polybasic acid by heating the residue from step (c), and (e) recycling the product of step (d) to step (a).

10. The process of claim 9 wherein the temperature of the reaction mixture in step (b) is maintained between 50° C. and 80° C.

11. The process of claim 9 in which between 0.4 and 1.10 mols of hydrogen peroxide is incorporated into the reaction mixture per mol of the olefin.

12. The process of claim 10 in which between 0.4 and 1.10 mols of hydrogen peroxide is incorporated into the reaction mixture per mol of the olefin.

13. The process of claim 9 wherein the cyclic anhydride of a polybasic acid is phthalic anhydride.

14. The process of claim 10 wherein the cyclic anhydride of a polybasic acid is phthalic anhydride.

15. The process of claim 11 wherein the cyclic anhydride of a polybasic acid is phthalic anhydride.

16. The process of claim 12 wherein the cyclic anhydride of a polybasic acid is phthalic anhydride.

* * * * *